United States Patent [19]

Gabrielli et al.

[11] Patent Number: 5,015,721

[45] Date of Patent: May 14, 1991

[54] THERMOTROPIC LIQUID-CRYSTALLINE AROMATIC, POLYESTERS

[75] Inventors: Giorgio Gabrielli, Milan; Mauro Maritano, Rovellasca; Giuseppe Motroni, Galliate; L. Lawrence Chapoy, Lesa, all of Italy

[73] Assignee: Montedison S.p.A., Milan, Italy

[21] Appl. No.: 433,411

[22] Filed: Nov. 7, 1989

Related U.S. Application Data

[63] Continuation of Ser. No. 277,126, Nov. 29, 1988, abandoned.

[30] Foreign Application Priority Data

Dec. 2, 1987 [IT] Italy ................................ 22854 A/87

[51] Int. Cl.$^5$ ...................... C08G 63/00; C08G 63/02
[52] U.S. Cl. ..................................... 528/190; 528/125; 528/128; 528/176; 528/191; 528/192
[58] Field of Search ............... 528/125, 128, 176, 190, 528/191, 192

[56] References Cited

U.S. PATENT DOCUMENTS 4,230,817 10/1980 Charbonnea ..................... 528/192
4,628,125 12/1986 Rogers et al. ..................... 562/488
4,654,412  3/1987 Calundann et al. ............... 528/192

Primary Examiner—Harold D. Anderson
Assistant Examiner—T. Mosley
Attorney, Agent, or Firm—Stevens, Davis, Miller & Mosher

[57] ABSTRACT

Thermotropic liquid-crystalline aromatic polyesters processable in the molten state, comprising units derived from at least one dicarboxy aromatic acid having the formula:

$$HOOC-Ar_1-O-Ar_2-COOH \qquad (1)$$

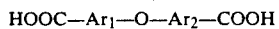

wherein $Ar_1$ and $Ar_2$ are aromatic radicals from aromatic diols, and, possibly, from other diacids and/or hydroxy acids.

10 Claims, No Drawings

THERMOTROPIC LIQUID-CRYSTALLINE AROMATIC, POLYESTERS

This application is a continuation of application Ser. No. 277,126, filed Nov. 29, 1988, now abandoned.

DESCRIPTION OF THE INVENTION

The present invention relates to thermotropic liquid-crystalline aromatic polyesters.

More particularly, the present invention relates to thermotropic liquid-crystalline aromatic polyesters easily processable in the molten state, and having the mesogen group in their main chain.

The use of synthetic polymers, both pure and in admixture with reinforcing agents, in order to manufacture articles having high mechanical properties, has rapidly spread during the past ten years.

In particular, the polyesters have proved to be particularly valuable for preparing injection-molded, or extruded products, such as films or fibers.

A class of polyesters endowed with better than average mechanical properties are those known as thermotropic liquid-crystalline polyesters.

In general, the thermotropic liquid-crystalline polymers show, in the molten state, and within a defined temperature range, an ordered arrangement of the molecular chains, which is retained in the solid state, thus securing to the polymer desirable properties, such as a high elastic modulus, a high tensile strength and, in general, the typical properties of a fiber-reinforced polymer.

Furthermore, these polymers may show a high crystallinity which gives the end products further advantageous properties, such as a lower heat distortion and a better resistance to attack by solvents.

Thermotropic liquid-crystalline polyesters, which hence show an optical anisotropy in the molten state, are described in the technical literature, such as, e.g., in: British Polymer Journal (Dec. 1980), page 154: "Liquid Crystal Polymer;" Journal of Macromolecular Science-Chemistry (1984), page 1705: "Liquid Crystalline Aromatic Polyesters;" Die Augewandte Makromolekulare Chemie (1982), 109–110, page 1: "Rigid Chain Polymers;" Die Augewandte Makromolekulare Chemie (1986), 145-46, page 231; "Thermotropic Liquid Crystalline Polymers;" Journal of Molecular Science Review (1986) C26(4), page 551: "Liquid Crystalline Polymers: A Novel State of Material."

The use of such polyesters makes possible high-tenacity fibers or molded articles to be obtained from the material in the molten state, such as, e.9., by injection-molding, which are endowed with suitable characteristics of stiffness, hardness and tenacity.

In accordance with the present invention, a novel class of polyesters have been discovered that are endowed with optical anisotropy in the molten state, which can be extruded to yield films or fibers, or molded to yield end articles, by using such technologies of fabrication as are commonly used for processing plastic materials.

Therefore, the object of the present invention are the thermotropic liquid-crystalline aromatic polyesters which comprise:

(a) at least one unit derived from dicarboxy aromatic acids of the formula:

$$HOOC-Ar_1-O-Ar_2-COOH \quad (1)$$

wherein:

$Ar_1$ represents a divalent aromatic radical consisting of one ring or a plurality of condensed, partially condensed or non-condensed rings, containing from 6 to 18 carbon atoms, and which may be substituted With halogens, or alkyl, aryl or aralkyl radicals containing a small number of carbon atoms; and $Ar_2$ represents a divalent aromatic radical consisting of a plurality of condensed, partially condensed or non-condensed rings, containing from 12 to 18 carbon atoms, and Which may be substituted With halogens, or alkyl, aryl or aralkyl radicals containing a small number of carbon atoms;

(b) at least one unit derived from aromatic diols of the formula:

$$HO-Ar_3-OH \quad (2)$$

wherein:

$Ar_3$ represents a divalent aromatic radical consisting of one ring, or of a plurality of condensed, partially condensed or non-condensed rings, containing from 6 to 18 carbon atoms, and which may be substituted with halogens, or with alkyl, aryl or aralkyl radicals containing a small number of carbon atoms, with cycloalkyl radicals containing from 5 to 12 carbon atoms, or with keto groups —COR or ether groups —OR, wherein R represents an alkyl radical, a cycloalkyl radical, an aryl radical consisting of one ring or of a plurality of condensed, partially condensed or non-condensed rings, containing from 1 to 18 carbon atoms, and which may be substituted with halogens or with alkyl, aryl or aralkyl radicals containing a small number of carbon atoms, and, if desired, at least one unit derived from other aromatic diacids and/or hydroxy acids, having the formulae:

$$(c) \; HOOC-Ar_3-COOH \quad (3)$$

$$(d) \; HO-Ar_3-(CH=CH)_n-COOH \quad (4)$$

wherein n has a value of either 0 or 1.

By the term "alkyl, aryl or aralkyl radicals containing a small number of carbon atoms," as used in the present specification and in the appended claims, alkyl radicals containing from 1 to 4 carbon atoms and aryl or aralkyl radicals containing from 6 to 12 carbon atoms are meant.

According to a preferred form of practical embodiment of the polyesters according to the present invention, at least 80 mol % of the products of the formulae (1), (2), (3) and (4) have both their functional groups in such positions as to form a polymeric chain with a substantially coaxial or parallel direction.

Prefered dicarboxy aromatic acids of formula [1) are those wherein $Ar_1$ is a unit selected from 1,4-phenylene; 4,4'-diphenylene; 2,6-naphthylene; 1,4-naphthylene; and $Ar_2$ is a unit selected from 4,4'-diphenylene; 2,6-naphthylene; and 1,4-naphthylene.

Examples of aromatic diols of the formula (2) are hydroquinone; chloro-bromo-hydroquinone; methyl, ethyl, propyl, tert.-butyl-hydroquinone; phenyl-hydroquinone; (1-phenyl-ethyl)-hydroquinone; (1-methyl-1-phenyl-ethyl)-hydroquinone; cyclohexyl-hydroquinone; benzoyl-hydroquinone; phenoxy-hydroquinone; 4,4'-dihydroxy-diphenyl; 3,3'-dichloro- 4,4'-dihydroxy-diphenyl; 3,3'-dimethyl-4,4'-dihydroxydiphenyl; 3,3'-dibromo-4,4'-dihydroxy-diphenyl; 3,3'-diphenyl-4,4'dihydroxy-diphenyl; 2,6-dihydroxy-naphthalene; 1,5-dihydroxy-naphthalene; 4,4'-dihydroxy-stilbene; and so forth.

Examples of dicarboxy aromatic acids having the formula (3) are terephthalic acid; chloro, bromo-terephthalic acid; methyl-terephthalic acid; 1,4-naphthalene-dicarboxy acid; 1,5-naphthalene-dicarboxy acid; 2,6-naphthalene-dicarboxy acid; 4,4'diphenylene-dicarboxy acid; 3,3'-dibromo-4,4'-diphenylene-dicarboxy acid; 4,4'-stilbene-dicarboxy acid; and so forth.

Examples of hydroxy acids having the formula (4) are p-hydroxy-benzoic acid; 3-chloro-4-hydroxy-benzoic acid; 3-bromo-hydroxy-benzoic acid; 3,5-dichloro-hydroxy-benzoic acid; 3-methyl-hydroxy-benzoic acid; 3-tert.-butyl-4-hydroxybenzoic acid; 4-hydroxy-1-naphthoic acid; 6-hydroxy-2-naphthoic acid; p-(4-hydroxyphenyl)-benzoic acid; p-hydroxycinnamic acid; and so forth.

According to a preferred form of practical embodiment of the thermotropic liquid-crystalline aromatic polyesters of the present invention, the units derived from the dicarboxy acids as defined under [a] and (c) are in molar ratios of (c)/(a) within the range of from 0 to 4, and the units derived from the hydroxy acids as defined under (d) are in molar ratios of (d)/(b), to the aromatic diols as defined under (b), within the range of from 0 to 3.

Thermotropic liquid-crystalline aromatic polyesters may also be those in Which the molar ratios of (c)/(a) and (d)/(b) are respectively Within the ranges of from 0.25 to 2 and of from 0.25 to 1.

The polyesters of the present invention are optically anisotropic in the molten state, as can be verified by means of optical microscopy analysis under polarized light, and have an inherent viscosity, measured in pentafluorophenol at 60° C, at a concentration of 0.25 g/liter, within the range of from 0.3 to 4 dl/g.

Their melting temperature may vary within wide limits, according to the composition of the polymer and the polymerization degree. Generally, hoWever, such melting temperature is within the range of from 250° to 350° C.

The molecular weight and the crystallinity may be increased by heating the polymer particles in an inert medium, or under vacuum, at a temperature just under the melting point, for sufficiently long time periods.

Such polymers are furthermore suitable for use in order to obtain fabricated or shaped bodies which may be prepared by the usual technologies of fabrication of thermoplatic polymers such as, e.g., by injection molding or extrusion. They may be processed to yield films or fibers; they may be used as matrices for composite materials based on inorganic fibers or fillers; and they may be used in blends with other polymers.

The preparation of the liquid-crystalline polymers according to the present invention may be carried out according to per se conventional techniques, by reacting the above mentioned units under the normal conditions of preparation of polyester resins.

The compounds as defined under (b), (c) and (d) are products per se known and available from the market, or they may be easily produced by the usual techniques as described in the technical literature, whilst the compounds of the formula (1) are novel products, have never been described in the technical literature, and may be obtained according to the following reaction scheme:

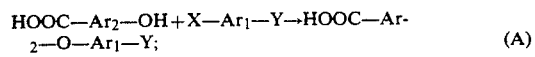  (A)

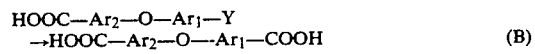  (B)

wherein:

$Ar_1$ and $Ar_2$ have the same meanings as stated above,

X may be a halogen, a nitro group, or any leaving group,

Y may be a —CN group, a —CON(W)$_2$ group, a —COOW group, or other electron-attracting groups which may be precursors of the carboxy group, and W is a ($C_1$-$C_4$)-alkyl radical.

The (A) reaction is a reaction of nucleophilic substitution, generally carried out at a temperature within the range of from 80° to 150° C, and in the presence of an aprotic solvent such as, e.g., dimethylformamide.

The (B) reaction is a normal hydrolysis reaction carried out at room temperature in an aqueous medium.

The product obtained is recovered from the hydrolysis reaction by means of precipitation, filtration and drying.

The thermotropic liquid-crystalline polyesters according to the present invention may be obtained in the molten state, or in the presence of a dispersing medium having a high boiling point, such as diphenyl-sulphone, or mixtures of particularly hydrogenated terphenyls, by transesterification between the dicarboxy aromatic acids and possibly the hydroxy acids, and the acetates or propanoates of the phenols, at temperatures within the range of from 270° to 370° C, so as to favor the complete release of the aliphatic acid. Operating under vacuum is also contemplated.

The reaction may, if desired, be carried out in the presence of a transesterification catalyst such as, e.g., phosphates of alkali or alkaline earth metals.

Further catalysts may be those which are commonly used in polycondensation processes, and are described in the "Encyclopaedia of Polymer Science and Technology" (1969, Vol. 10, pages 722-723).

Examples of such catalysts are the oxides, hydroxides, hydrides, halides, alkoxides or phenates, the salts and the complex salts of the organic or inorganic acids of lithium, sodium, potassium, magnesium, calcium, titanium, manganese, cobalt, zinc, tin, antimony, lanthanum, cerium, lead and germanium.

The required amount of catalyst is within the range fo from 0.005 to 1% by mol, and is preferably within the range of from 0.01 to 0.2% mol, calculated on the total amount of the reactants.

According to an alternative method, the liquid-crystalline polyesters of the present invention may be obtained in solution, by polycondensation between the halides of the dicarboxy aromatic acids and the mixture of the phenols in a suitable solvent. The temperature is within the range of from 25° to 220° C, and the reaction is carried out in the presence of a base and/or of a stream of nitrogen in order to favor the elimination of the hydrogen halide.

Among the bases, pyridine is preferred, whilst among the solvents, the chlorinated, both aliphatic and aromatic, solvents, are preferred, such as methylene chloride, chlorobenzene, dichloro-benzenes, and trichloro-benzenes.

The polymer obtained by this second method is subsequently recovered by evaporating the solvent, or by precipitation with a non-solvent, and subsequent filtration.

In order still better to understand the present invention and to practice it, some illustrative nonlimitative examples are reported below.

EXAMPLE 1

Preparation of 6-(4'-carboxy-phenoxy)-2-naphthoic acid

To a 3-neck flask of 1 liter capacity equipped with mechanical stirring means, reflux condenser and thermometer, the following reactants are charged under a nitrogen stream:
7.5 g of para-nitro-benzonitrile (50.7 mM);
9.5 g of 6-hydroxy-2-naphthoic aoid (53.Z mM);
8.5 g of anhydrous potassium carbonate (85 mM); and
500 ml of anhydrous dimethyl-formamide.

The reaction mixture is.stirred and heated at 100° C. for 6 hours, and is then poured into Water (2 liters) and acidified to pH 3 by hydrochloric acid.

A brown precipitate is obtained, and is recrystallized from acetone/water. Yield: 8.81 g (60%).

This product is hydrolysed in a solution consisting of water (180 ml), methyl-cellosolve (60 ml), and sodium hydroxide (60 g), under refluxing conditions for 4 hours. At the end, the obtained product is recovered by dilution with water, acidification with HCl, precipitation, filtration, and drying.

The product is purified by crystallization from acetic acid/$H_2O$, its HPLC purity showing it to be higher than 99%, and its structure being confirmed by means of massspectrometry. The yield is 82%.

EXAMPLE 2

The polymerization equipment is a 3-neck flask of 100 ml capacity equipped with stirring means, nitrogen inlet tube, and distillation head with condenser.

The equipment is heated by means of a high-temperature silicone oil bath.

To this reactor, the following reactants are charged:
6.00 g of 6-(4'-carboxy-phenoxy)-2-naphthoic acid (19.5 mM);
(b) 4.05 g of 2-methyl-hydroquinone diacetate (19.5 mM); and
(c) 0.060 g of tribasic sodium phosphate dodecahydrate.

Under a slight nitrogen stream, the reaction mixture is heated for 30 minutes at 200° C., then for 30 minutes at 240° C., for 30 minutes at 260° C., for 1 hour at 280° C., for 1 hour at 300° C., and finally for a further 1 hour at 300° C. under a vacuum of 0.5-1 millibars. During the whole process, the distilled acetic acid is removed from the reaction.

The reaction mass, after cooling to room temperature, is recovered, weighed and finely ground.

The polymer, which is in the form of a powder with a light beige color, has an inherent viscosity (at 0.25% in pentafluorophenol at 60° C.) of 0.5 dl/g, and, when subjected to DSC (Differential Scanning CalorimetrY) analysis, shows an endothermic peak at 280° C., which is repeated during the subsequent cooling/heating cycles. In the cooling cycle (20° C./minute), an exothermic peak at 250° C. is detected, which indicated a quick crystallization.

The polymer, when examined under polarized light on the microscope equipped with heated stage, shows, at temperatures higher than 280° C., strong phenomena of light birefringence, correlated with the anisotropic nature of the polymer in the molten state.

EXAMPLE 3

In the same equipment and with the same procedures as in Example 2, the following reactants are polymerized:
(a) 6.00 g of 6-(4'-carboxy-phenoxy)-2-naphthoic acid (19.5 mM);
(b) 4.47 g of 2-chloro-hydroquinone diacetate (19.5 mM); and
(c) 0.060 g of tribasic sodium phosphate dodecahydrate.

The polymer obtained has an inherent viscosity of 0.51 dl/g and, when subjected to DSC analysis, shows a melting point of 267° C., and a crystallization temperature of 246° C.

The molten polymer is optically anisotropic when examined under the polarized-light microscope.

EXAMPLE 4

In the same equipment and with the same procedures as disclosed in Example 2, the following reactants are polymerized:
(a) 6.00 g of 6-(4'-carboxy-phenoxy)-2-naphthoic acid (19.5 mM);
1.89 g of hydroquinone diacetate (9.75 mM);
(c) 2.03 g of 2-methyl-hydroquinone diacetate (9.75 mM); and
(d) 0.01 g of tribasic sodium phosphate dodecahydrate.

The polymer thus obtained has an intrinsic viscosity of 1.12 dl/g and, when subjected to DSC analysis, shows a melting endothermic peak at 356° C., which is repeated during the subsequent cooling/heating cycles. In the cooling cycle, an exothermic peak is evidenced at 316° C., showing a quick crystallization.

When observed under the polarized-light microscope, the polymer proves to be birefringent in the molten rate.

What is claimed is:

1. A thermotropic liquid-crystalline aromatic polyester which comprises:
   (a) at least one unit derived from dicarboxy aromatic acids of the formula:

$$HOOC-Ar_1-O-Ar_2-COOH \qquad (1)$$

wherein;
   $Ar_1$ represents a divalent aromatic radical consisting of one ring, or of a plurality of condensed, partially condensed or non-condensed rings, containing from 6 to 18 carbon atoms, optionally substituted with halogens, or alkyl, aryl or aralkyl radicals containing a small number of carbon atoms; and
   $Ar_2$ represents a divalent aromatic radical consisting of a plurality of condensed, partially condensed or non-condensed rings, containing from 12 to 18 carbon atoms, optionally substituted with halogens, or alkyl, aryl or aralkyl radicals containing a small number of carbon atoms;
   (b) at least one unit derived from aromatic diols of the formula:

$$HO-Ar_3-OH \qquad (2)$$

wherein:
   $Ar_3$ represents a divalent aromatic radical consisting of one ring, or of a plurality of condensed, partially condensed or non-condensed rings, containing from 6 to 18 carbon atoms, optionally substituted with halogens or with alkyl, aryl, or aralkyl radicals containing a small number of carbon atoms, with cycloalkyl radicals containing from 5 to 12 carbon atoms, or with keto groups —COR or either groups —OR, wherein R represents an alkyl radical, or a cycloalkyl radical, an aryl radical consisting of one ring or of a plurality of condensed, partially condensed or non-condensed rings, containing from 1 to 18 carbon atoms, optionally substituted with halogens or with alkyl, aryl, or aralkyl radicals containing a small number of carbon atoms.

with or without at least one unit derived from other aromatic diacids hydroxy acids on both having the formula:

(c) HOOC—Ar$_3$—COOH  (3)

(d) HO—Ar$_3$—(CH=CH)$_n$—COOH  (4)

wherein n has a value of either 0 or 1.

2. A polyester according to claim 1, wherein at least 80 mol % of the compound of the formula (1), (2), (3), and (4) have both their functional groups in such positions as to form a polymeric chain with a substantially coaxial or parallel direction.

3. A polyester according to claim 1, wherein the dicarboxy aromatic acids of formula (1) are those wherein Ar$_1$ is a unit selected from the closs consisting of 1,4-phynylene; 4,4'-diphenylene; 2,6-naphthylene; and Ar$_2$ is a unit selected from the class consisting of 4,4'-diphenylene; 2,6-naphthylene; and 1,4 naphthylene.

4. A polyester according to claim 1, 2, or 3, wherein the aromatic diols are selected from the class consisting of hydroquinone; chloro, bromo-hydroquinone; methyl, ethyl, propyl, tert.-butyl-hydroquinone; phenyl-hydroquinone; (1-phenyl-ethul)-hydroquinone; (1-methyl-1-phenyl-ethyl)-hydroquinone; cyclohexyl-hydroquinone; benzoyl-hyroquinone; phenoxy-hydroquinone; 4,4'-dihydroxy-diphenyl; 3,3'-dibromo-4,4'-dihydroxy; 3,3'-dichloro-4,4'-dihydroxy-diphenyl-4,4'-dihydroxy-diphenyl; 2,6-dihydroxy-naphthalene; 1,5-dihydroxy-naphthalene; and 4,4'-dihydroxy-stilbene.

5. Polyesters according to claims 1, 2, or 3 wherein the aromatic diacids having the formula (3) are selected from the class consisting of terephthalic acid; chloro, bromo-terephthalic acid; methyl-terephthalic acid; 1,4-naphthalene-dicarboxy acid; 1-5naphthalene-dicarboxy acid; 2,6-naphthalene-dicarboxy acid; 4,4'-diphenylene-dicarboxy acid; 3,3'-dibromo-4,4'-diphenylene-dicarboxy acid; and 4,4'-stilbene-dicarboxy acid.

6. A polyester according to claim 1, 2, or 3, wherein the hydroxy acids are selected from the class consisting of p-hydroxy-benzoic acid; 3-chloro-4-hydroxy-benzoic acid; 3-bromo-4-hydroxy-benzoic acid; 3,5-dichloro-4-hydroxy-benzoic acid; 3-methyl-4-hydroxy-benzoic acid; 3-tert.-butyl-4-hydroxy-benzoic acid; 4-hydroxy-1-naphthoic acid; 6-hydroxy-2-naphthoic acid; p-(4-hydroxy-phenyl)-benzoic acid; and p-hydroxycinnamic acid.

7. A polyester according to claim 1, 2 or 3 wherein the units derived from the dicarboxy acids as defined under (a) and (c) are in mutual molar ratios of (c)/(a) within the range of from 0 to 4, and wherein the units derived from the hydroxy acids as defined under (d) are in molar ratios of (d)/(b) to the aromatic diols as defined under (b), which are within the range of from 0 to 3.

8. A polyester according to claim 7, wherein the molar ratios of (c)/(a) and (d)/(b) are respectively within the ranges of from 0.25 2 and of from 0.25 to 1.

9. A polyester according to claim 1, 2 or 3, having an inherent viscosity, measured in pentafluorophenl at 60° C., at a concentration of 0.25 g/liter, within the range of from 0.3 to 4 dl/g, and a melting temperature within the range of from 250° to 350° C.

10. A fiber, a film, or a shaped article formed by injection or extrusion, or as a matrix for composite materials based on inorganic fibers or fillers made of a polyester as defined in claim 1, 2, or 3.

* * * * *